United States Patent [19]

Sullivan, Jr.

[11] 3,936,495
[45] Feb. 3, 1976

[54] PURIFICATION PROCESS
[75] Inventor: Alan P. Sullivan, Jr., Lebanon, N.J.
[73] Assignee: Merck & Co., Inc., Rahway, N.J.
[22] Filed: Nov. 27, 1973
[21] Appl. No.: 419,304

[52] U.S. Cl............................ 260/501.12; 260/519
[51] Int. Cl.². ...................................... C07C 143/28
[58] Field of Search........... 260/501.12, 501.11, 519

[56] References Cited
UNITED STATES PATENTS

| | | | |
|---|---|---|---|
| 2,681,927 | 6/1954 | McCollum et al. | 260/501.11 |
| 3,211,791 | 10/1965 | Druey et al. | 260/501.12 |
| 3,462,536 | 8/1969 | Chemerda et al. | 424/309 |
| 3,515,749 | 6/1970 | Fried et al. | 260/501.11 |
| 3,725,470 | 4/1973 | Bretschneider et al. | 260/519 |
| 3,769,424 | 10/1973 | Bayne | 424/317 |

Primary Examiner—Bernard Helfin
Assistant Examiner—Nicky Chan
Attorney, Agent, or Firm—Harry E. Westlake, Jr.; Francis H. Deef

[57] ABSTRACT

The p-toluene sulfonic acid addition salt of α-hydrazino-α-methyl-β-(3,4-dihydroxyphenyl)propionic acid is formed to readily allow crystallization of the product from solution. The acid addition salt may be dissolved and then neutralized to obtain the free base in pure form.

2 Claims, No Drawings

PURIFICATION PROCESS

The present invention relates to a novel and useful process for purifying α-hydrazino-α-methyl-β-(3,4-dihydroxyphenyl)propionic acid by the formation of an intermediate acid addition salt. The acid addition salt may be dissolved and then neutralized to obtain the free base in an even more pure form. More particularly, it relates to the p-toluene sulfonic acid salt of α-hydrazino-α-methyl-β-(3,4-dihydroxyphenyl)propionic acid.

It is known in the art that α-hydrazino-α-methyl-β-(3,4-dihydroxyphenyl)propionic acid is a very potent decarboxylase inhibitor (see U.S. Pat. No. 3,462,536). It is further known in the art that such decarboxylase inhibitors are useful in combination with L-dopa in the treatment of Parkinsons disease (see U.S. Pat. No. 3,769,424). It is still further known that the D-isomer of α-hydrazino-α-methyl-β-(3,4-dihydroxyphenyl)-propionic acid is inactive and that it is preferred to use a composition containing the L-isomer rather than the racemic mixture (see British Pat. No. 1,261,660). Since the products are to be used for pharmaceutical purposes, it is obvious that they should be obtained in as pure a form as is possible. However, when such compounds are formed, it is inherent that there be some minor amounts of impurities. In many instances such impurities can be removed by simple crystallization of the acid addition salts of the compounds. With the present compounds many acid addition salts have been tried but many formed gums or glasses and do not crystallize from solution. For example, the acid addition salts formed with hydrochloric acid, sulfuric acid and phosphoric acid will not crystallize from solution. Quite obviously, if a relatively simple acid addition salt could be formed with crystallized readily from solutions, it would represent a substantial advancement in the purification of such compounds.

Furthermore, due to a breakdown in equipment or mismeasurement etc., it sometimes happens that quality control detects pills, capsules, etc. which are either subpotent or super-potent. In such instances, it is desirable to recover the α-hydrazino-α-methyl-β-(3,4-dihydroxyphenyl)-propionic acid since it represents an expensive component of the composition. Obviously, if a simple purification step would allow such recovery, it would represent an advancement in the art.

It is an object of the present invention to provide an acid addition salt of racemic of L-α-hydrazino-α-methyl-β-(3,4-dihydroxyphenyl)propionic acid which will readily crystallize from solution. A further object is to provide a process for purifying racemic or L-α-hydrazino-α-methyl-β-(3,4-dihydroxyphenyl)propionic acid. A still further object is to provide a purification process which can be carried out on either a laboratory or industrial scale. Other objects will become apparent as the description of the invention proceeds.

These objects are accomplished by the present invention which provides the p-toluene sulfonic acid addition salt of α-hydrazino-α-methyl-β-(3,4-dihydroxyphenyl)propionic acid. In a preferred embodiment of the present invention, the α-hydrazino-α-methyl-β-(3,4-dihydroxyphenyl)propionic acid is in the L-stero configuration rather than being a racemic mixture.

The present invention further provides a process for purifying α-hydrazino-α-methyl-β-(3,4-dihydroxyphenyl)-propionic acid which comprises dissolving said compound in an inert solvent, reacting said compound with at least about a 0.8 mole ratio of p-toluene sulfonic acid and thereafter precipitating the p-toluene sulfonic acid addition salt of α-hydrazino-α-methyl-β-(3,4-dihydroxyphenyl)propionic acid from the solution.

In a preferred embodiment of the present invention, the inert solvent is water or ethyl acetate which is merely heated to dissolve the compound and then cooled to precipitate the acid salt.

The present invention also provides a still further purification process wherein the p-toluene sulfonic acid addition salt of α-hydrazino-α-methyl-β-(3,4-dihydroxyphenyl)propionic acid is dissolved in an inert solvent and neutralized to give α-hydrazino-α-methyl-β-(3,4-dihydroxyphenyl)propionic acid as the free base. Preferably the free base is in the L-stereo configuration.

The term "dissolving" is used in its broadest sense to mean that at least part of the compound is dissolved in the solvent. It should be noted however that not all of the compound need be dissolved and that the purification process can be carried out with slurrys or suspensions of the compound. The "inert solvents" which may be used in the practice of the present invention include water, alkanols of from 1 to 5 carbon atoms, ethyl acetate, acetone and other such obvious solvents. While it is preferred that water or ethyl acetate be used as the solvent, many other solvents may likewise be used. Water and ethyl acetate are preferred because when heated they readily dissolve the acid addition salt or the free base and when cooled the acid addition salt or the free base readily precipitates from the solution. Ethanol is a suitable solvent but the final materials of each step are quite soluble in ethanol and it is generally preferred to precipitate the acid addition salt or the free base by the addition of ethyl acetate and a stripping of the ethanol from the solution. In other instances a second solvent may be mixed with the first solvent to force the precipitation of the final product, i.e. either the acid addition salts or the free base. In any event, such precipitation procedures are well known in the art.

When carrying out the formation of the acid addition salt in solution, it is preferred that an excess of the p-toluene sulfonic acid be employed to insure as complete a recovery as is possible of the α-hydrazino-α-methyl-β-(3,4-dihydroxyphenyl)propionic acid. In general, from about 0.8 to about 3, more preferably from about 1 to about 2, moles of p-toluene sulfonic acid will be employed for each mole of racemic of L-α-hydrazino-α-methyl-β-(3,4-dihydroxyphenyl)propionic acid. As a practical matter, from about 1.2 to about 1.7 moles of p-toluene sulfonic acid are employed.

The following examples are given to illustrate the invention and are not intended to limit it in any manner. All parts are given in parts be weight unless otherwise expressed.

EXAMPLE 1

A. Preparation of p-toluene sulfonic acid addition salt of L-α-hydrazino-α-methyl-β-(3,4-dihydroxyphenyl)propionic acid

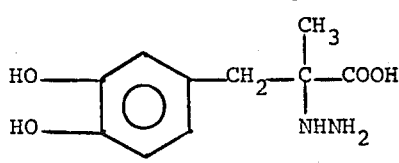 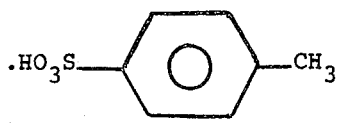

$C_{17}H_{22}N_2O_7S$, M.W. 398.43

2572 g. (10.5 moles) L-α-hydrazino-α-methyl-β-(3,4-dihydroxyphenyl)propionic acid
3000 g. (15.8 moles) p-toluene sulfonic acid monohydrate
12.6 l. water The above hydrazine compound is slurried in 12.6 l. of water under nitrogen. The p-toluene sulfonic acid is added all at once. The mixture is warmed to 30°–40°C. to from a solution. Crystallization occurs rapidly. The crystalline mixture is aged two hours at room temperature, then is chilled to 5°C. and aged at 0°–5°C. for one hour. The product is filtered and washed once with cold mother liquors. The product is dried in vacuo (20 mm.) at 40°C. Yield 3931 g., 94 percent of theory.

B. Preparation of L-α-hydrazino-α-methyl-β-(3,4-dihydroxyphenyl)propionic acid

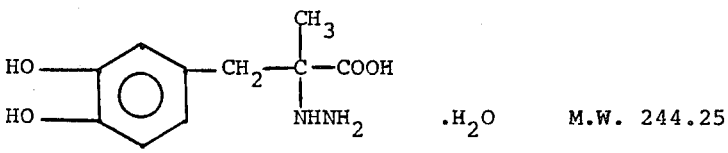 .$H_2O$    M.W. 244.25

20 g. (0.0503 moles) P-toluene sulfonic acid salt of L-α-hydrazino-α-methyl-β-(3,4-dihydroxyphenyl)-propionic acid
300 ml. water
4 ml. ammonium hydroxide The salt is dissolved in the water under nitrogen. The solution is filtered. The pH is adjusted from 1.6 to 2.0 with approximately 3 ml. of ammonium hydroxide. The precipitating L-α-hydrazino-α-methyl-β-(3,4-dihydroxyphenyl)-propionic acid is aged with stirring for 30 minutes. The pH is adjusted to 3.0 –3.5 with approximately 1 ml. of ammonium hydroxide and the slurry is again aged for 30 minutes. The product is chilled in an ice bath for 3 hours. The product is filtered, washed four times with ice water and dried in vacuo (20 mm.) at 40°–45°C. Yield 11.38 g., 93 percent theory. The product is analytically pure.

EXAMPLE 2

A. Preparation of p-toluene sulfonic acid salt of L-α-hydrazino-α-methyl-β-(3,4-dihydroxyphenyl)propionic acid A slurry is formed with 5.0 g. (0.025 moles) of L-α-hydrazino-α-methyl-β-(3,4-dihydroxyphenyl)propionic acid in 50 ml. of ethyl acetate under nitrogen. The slurry is heated to 70°C. and 4 g. (0.028 moles) of p-toluene sulfonic acid monohydrate is added all at once. The mixture which has cooled somewhat is reheated to 70°C. and then allowed to cool to room temperature. The mixture is aged 2½ hours at room temperature. The product is filtered, washed once with ethyl acetate and then dried in vacuo (20 mm.) at room temperature. The p-toluene sulfonic acid salt of L-α-hydrazino-α-methyl-β-(3,4-dihydroxyphenyl)propionic acid is obtained in a yield of 7.84 g. or 82 percent of theory.

B. Preparation of L-α-hydrazino-α-methyl-β-(3,4-dihydroxyphenyl)propionic acid The procedure of Example 1B is repeated utilizing the above salt. The results obtained are substantially as in Example 1B.

EXAMPLE 3

The procedure of Examples 1A and 1B is repeated with the exception that in place of the pure L-α-hydrazino-α-methyl-β-(3,4-dihydroxyphenyl)propionic acid there is employed first the racemate of α-hydrazino-α-methyl-β-(3,4-dihydroxyphenyl)propionic acid and secondly a mixture of broken tablets containing fillers, etc. as well as the L-α-hydrazino-α-methyl-β-(3,4-dihydroxyphenyl)propionic acid. With both starting materials substantially the same results are obtained with the exception that when a racemic product is employed a purified racemic product is the end product.

Many other equivalent modifications will be apparent to those skilled in the art from a reading of the foregoing without a departure from the inventive concept.

What is claimed is:
1. The p-toluene sulfonic acid addition salt of α-hydrazino-α-methyl-β-(3,4-dihydroxyphenyl)propionic acid.
2. The p-toluene sulfonic acid addition salt of L-α-hydrazino-α-methyl-β-(3,4-dihydroxyphenyl)propionic acid.

* * * * *